United States Patent
Sugimoto (10) Patent No.: US 7,242,189 B2
(45) Date of Patent: Jul. 10, 2007

(54) MAGNETIC RESONANCE DIAGNOSIS APPARATUS USING THREE-DIMENSIONAL MAGNETIC TAGGING METHOD

(75) Inventor: Hiroshi Sugimoto, Utsunomiya (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/865,797

(22) Filed: Jun. 14, 2004

(65) Prior Publication Data

US 2004/0222793 A1 Nov. 11, 2004

Related U.S. Application Data

(63) Continuation-in-part of application No. PCT/JP02/13023, filed on Dec. 12, 2002.

(30) Foreign Application Priority Data

Dec. 12, 2001 (JP) ............... 2001-378012

(51) Int. Cl.
*G01V 3/00* (2006.01)
(52) U.S. Cl. .................................... 324/307
(58) Field of Classification Search ............... 324/307, 324/309, 318
See application file for complete search history.

(56) References Cited

U.S. PATENT DOCUMENTS

| | | | | |
|---|---|---|---|---|
| 4,803,431 A | * | 2/1989 | Sano et al. | 324/306 |
| 5,111,820 A | | 5/1992 | Axel et al. | |
| 5,652,513 A | * | 7/1997 | Liu et al. | 324/306 |
| 5,722,411 A | * | 3/1998 | Suzuki et al. | 600/439 |
| 6,295,464 B1 | * | 9/2001 | Metaxas | 600/407 |
| 6,549,008 B1 | * | 4/2003 | Anand et al. | 324/307 |
| 6,564,080 B1 | * | 5/2003 | Kimura | 600/410 |
| 6,597,937 B2 | * | 7/2003 | Liu et al. | 600/420 |
| 6,624,630 B1 | * | 9/2003 | Foxall | 324/307 |
| 2002/0000805 A1 | * | 1/2002 | Kuhara | 324/306 |
| 2003/0171671 A1 | * | 9/2003 | Miyazaki | 600/420 |

FOREIGN PATENT DOCUMENTS

JP 2-291841 12/1990

(Continued)

OTHER PUBLICATIONS

William S. Kerwin, Jerry L. Prince, A k-Space Analysis of MR Tagging, Journal of Magnetic Resonance, Feb. 2000, vol. 142, No. 2, pp. 313-322.

(Continued)

*Primary Examiner*—Diego Gutierrez
*Assistant Examiner*—Dixomara Vargas
(74) *Attorney, Agent, or Firm*—Nixon & Vanderhye P.C.

(57) ABSTRACT

A magnetic resonance diagnosis apparatus is capable of performing magnetic tagging of a three-dimensional region to visualize three-dimensional motion or to quantitatively handle the motion. In this apparatus, a control unit controls a gradient magnetic field power source of each axis so that magnetization by gradient magnetic fields generated from a gradient magnetic field coil describes a three-dimensional orbit inside space and performs magnetic tagging for a predetermined three-dimensional region of an object by adjusting a magnitude of gradient magnetic field pulses, pulse intervals and application times. Consequently, one can provide an MRI apparatus capable of more flexibly observing motion of organs and flow of blood.

21 Claims, 7 Drawing Sheets

FOREIGN PATENT DOCUMENTS

WO          00/64344       11/2000
WO          02/02311        3/2002

OTHER PUBLICATIONS

Amir A. Amini, Yashing Chen, Mohamed Elayyadi, Petia Radeva, Tag Surface Reconstruction and Tracking of Myocardial Beads from SPAMM-MRI with Parametric B-Spline Surfaces, IEEE Transactions on Medical Imaging, Feb. 2001, vol. 20, No. 2, pp. 94-103.

* cited by examiner

MAGNETIC RESONANCE DIAGNOSIS APPARATUS USING THREE-DIMENSIONAL MAGNETIC TAGGING METHOD

This application is a continuation-in-part of PCT International Application No. PCT/JP02/13023 filed 12 Dec. 2002. PCT/JP02/13023 claims priority to JP Application No. 2001-378012 filed 12 Dec. 2001. The entire contents of these applications are incorporated herein by reference.

TECHNICAL FIELD

This invention relates to a magnetic resonance diagnosis apparatus. More particularly, the invention relates to a magnetic resonance diagnosis apparatus using a three-dimensional magnetic tagging method.

BACKGROUND ART

An imaging method known as the "magnetic tagging method" has been used in recent years to visualize organs in motion, such as the heart, and blood flow using a magnetic resonance diagnosis apparatus (hereinafter called an "MRI apparatus"). This method transmits a radio frequency magnetic field to a part of regions (ordinarily a belt-like or linear region) of an imaging region of an object and lets it get into magnetic saturation so that magnetic resonance signals (hereinafter called "MR signals") are generated from the belt-like or linear region, then applies a radio frequency magnetic field, gradient magnetic fields, etc, to the imaging region and performs imaging.

Incidentally, the technique of applying the radio frequency magnetic field to a part of the imaging region prior to imaging and bringing the part of the regions into magnetic saturation will be hereinafter called "magnetic tagging".

The MR signals are not generated or are generated only weakly during imaging in the region that is magnetically tagged and this region is displayed as non-signals or low signals on the image that is later re-constructed. When the region magnetically tagged is a region having less motion, display of the non-signal or the low signal is made as such in the belt-like or linear form, but is displayed in deviation on the image when the region magnetically tagged is a region having motion. This deviation varies depending on a moving distance during the period from magnetic tagging to imaging. Therefore, when magnetic tagging is executed for a region having fast motion, the deviation on the image becomes great, the motion can be visualized and the moving distance can be calculated, too.

Magnetic tagging of this kind is described in JP-A-1-47912, L. Axel et al "Radiology", Vol. 171, p. 841-845 (1989) and W. Kerwin et al "Journal of Magnetic Resonance" Vol. 142, p.313-322 (2000).

However, these prior art technologies two-dimensionally perform magnetic tagging and it is therefore difficult to visualize three-dimensional motion of the organs and to conduct quantitative measurement such as calculation of the moving distance.

Importance of magnetic tagging in three-dimensional regions will be described. Contraction and dilatation of the heart, for example, are performed while each tissue of the heart moves in a three-dimensional space but not on a two-dimensional plane. Because each tissue of the heart thus exhibits three-dimensional motion, the heart exhibits contraction and dilatation with twist as a whole.

To visualize such three-dimensional motion or to quantitatively handle the motion, magnetic tagging of the three-dimensional region is of utmost importance. This also holds true not only for motion of the heart but also for other organs and blood.

It is therefore an object of the invention to provide an MRI apparatus that can solve the problems described above and can more flexibly observe the motion of the organs and the blood.

SUMMARY OF THE INVENTION

To reduce the problems described above, the magnetic resonance diagnosis apparatus according to an exemplary embodiment of the invention is so constituted as to be capable of performing three-dimensional tagging.

More concretely, one aspect of the invention includes static magnetic field generation means for generating a static magnetic field applied to an object; gradient magnetic field generation means for generating gradient magnetic fields applied to the object; radio frequency magnetic field generation means for generating a radio frequency magnetic field applied to the object; and control means for controlling the gradient magnetic fields generated from the gradient magnetic field generation means and the radio frequency magnetic field generated from the radio frequency magnetic field. The control means includes magnetic tagging means for controlling the gradient magnetic fields generated from the gradient magnetic field generation means such that magnetization inside the object due to the gradient magnetic fields generated from the gradient magnetic field generation means describes a three-dimensional movement orbit inside a k-space, and for performing magnetic tagging for a predetermined region of the object, and signal collection means for collecting MR signals from a region of the object inclusive of the three-dimensional region after magnetic tagging by the magnetic tagging means.

In one of the embodiments, the magnetic tagging means described above controls the gradient magnetic fields so that the radio frequency magnetic field generated from the radio frequency magnetic field generation means can be kept at a predetermined intensity while the gradient magnetic fields are controlled.

Further, the magnetic tagging means controls the gradient magnetic fields generated from the gradient magnetic field generation means so that the magnetization describes an orbit moving on predetermined sides of a substantial cube, a substantial rectangle, a polyhedron, etc, in the k-space.

According to another embodiment of the invention, the control means particularly includes magnetic tagging means for controlling the gradient magnetic field generation means and the radio frequency magnetic field in such a fashion as to perform magnetic tagging for a predetermined three-dimensional region of the object, and signal collection means for collecting MR signals from a region of the object inclusive of the three-dimensional region after magnetic tagging by the magnetic tagging means.

According to still another embodiment of the invention, there is provided a magnetic resonance signal collection method for collecting MR signals from an object placed in a static magnetic field by applying gradient magnetic fields and a radio frequency magnetic field to the object. This method includes the steps of controlling the gradient magnetic fields and the radio frequency magnetic field, performing magnetic tagging for a predetermined three-dimensional region of the object, and collecting the MR signals from a region of the object inclusive of the three-dimensional region after magnetic tagging is conducted.

According to still another embodiment of the invention, there is provided a computer-readable program for magnetic resonance diagnosis including the steps of causing a magnetic resonance diagnosis apparatus to perform magnetic tagging for a predetermined three-dimensional region of an object, and causing the magnetic resonance diagnosis apparatus to collect MR signals from a region inclusive of the three-dimensional region magnetically tagged.

DETAILED DESCRIPTION OF EXEMPLARY EMBODIMENTS

First Embodiment

The first embodiment of the invention will be explained hereinafter in detail with reference to the drawings.

Figure 1:
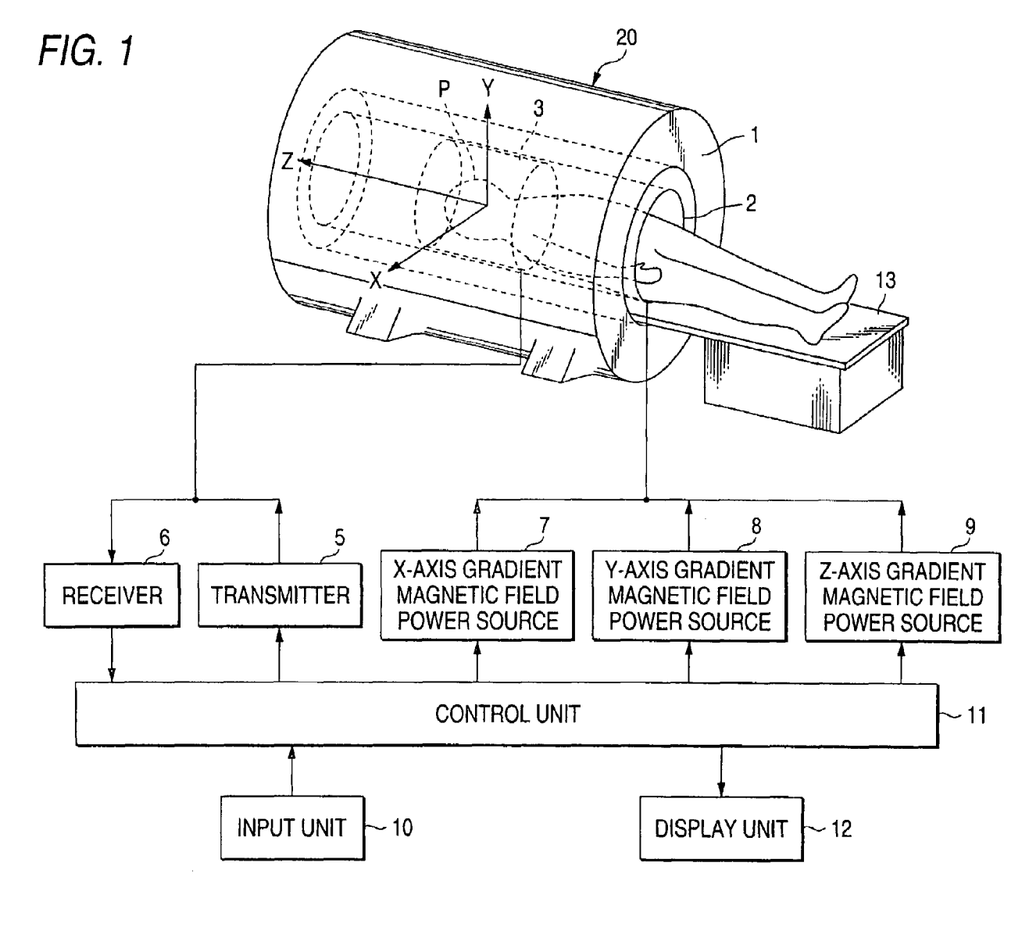
FIG. 1 is a block diagram showing a schematic construction of an MRI apparatus according to a first embodiment of the invention.

FIG. 1 is a block diagram showing a schematic construction of an MRI apparatus according to the first embodiment of the invention. A static magnetic field magnet 1, an X-Y-Z axes gradient magnetic field coil 2 and a transmission/reception coil 3 are arranged inside a cylindrical gantry 20. Here, the Z axis is coincident with a longitudinal center line of the cylinder, the X axis extends in a horizontal direction and the Y axis does in a vertical direction.

The static magnetic field magnet 1 as a static magnetic field generator is constituted by use of a super-conducting magnet, for example, and is a magnet that applies a magnetic field of 1.5T, for example, to an object P. The X-Y-Z axes gradient magnetic field coil 2 is arranged inside the static magnetic field magnet 1, has cylindrical assemblies and generates an X-axis gradient magnetic field, a Y-axis gradient magnetic field and a Z-axis magnetic field, respectively.

Incidentally, the shape of each assembly and its type are not limited. The transmission/reception coil 3 is arranged inside the gradient magnetic field coil 2, has a cylindrical shape, for example, and generates a radio frequency magnetic field or detects an MR signal generated by magnetic resonance. Incidentally, a bed 13 has a ceiling plate. The object P put onto the ceiling plate is loaded into an imaging space (a spherical region in which an imaging magnetic field is generated) inside the gantry 20.

The X-Y-Z axes gradient magnetic field coil 2 is connected to a control unit 11 through an X-axis gradient magnetic field power source 7, a Y-axis gradient magnetic field power source 8 and a Z-axis gradient magnetic field power source 9.

The X-axis gradient magnetic field power source 7, the Y-axis gradient magnetic field power source 8 and the Z-axis gradient magnetic field power source 9 supply electric power necessary for generating the magnetic fields from the X-Y-Z axes gradient magnetic field coil 2. The magnitude of power (intensity of the magnetic field), the timing of the supply of power (application timing of the magnetic fields), and so forth, are controlled from control signals from the control unit 11.

The transmission/reception coil 3 is connected to the control unit 11 through a transmitter 5 and a receiver 6. The transmitter 5 is driven when a radio frequency magnetic field is transmitted from the transmission/reception coil 3 to the object P and the receiver 6 is driven when the MR signals are detected from the object P through the transmission/reception coil 3.

A display unit 12 is connected to the control unit 11 and displays an MR image of the object P.

Next, the operation of the MRI apparatus according to this embodiment will be explained.

An operator inputs to report that a magnetic tagging method is used to the control unit 11 through an input unit 10 by performing a predetermined operation and then loads the object P into the imaging region inside the gantry 20. When the predetermined instruction is given, the control unit 11 reads out a program used for the magnetic tagging method from a predetermined built-in memory (not shown in the drawing). This program describes information of control signals for executing magnetic tagging and a procedure for magnetic tagging and imaging. The control unit 11 transmits predetermined control signals (hereinafter called "pulse sequence") to the transmitter 5, the X-axis gradient magnetic field power source 7, the Y-axis gradient magnetic field power source 8 and the Z-axis gradient magnetic filed power source 9 on the basis of this program.

Figure 2:
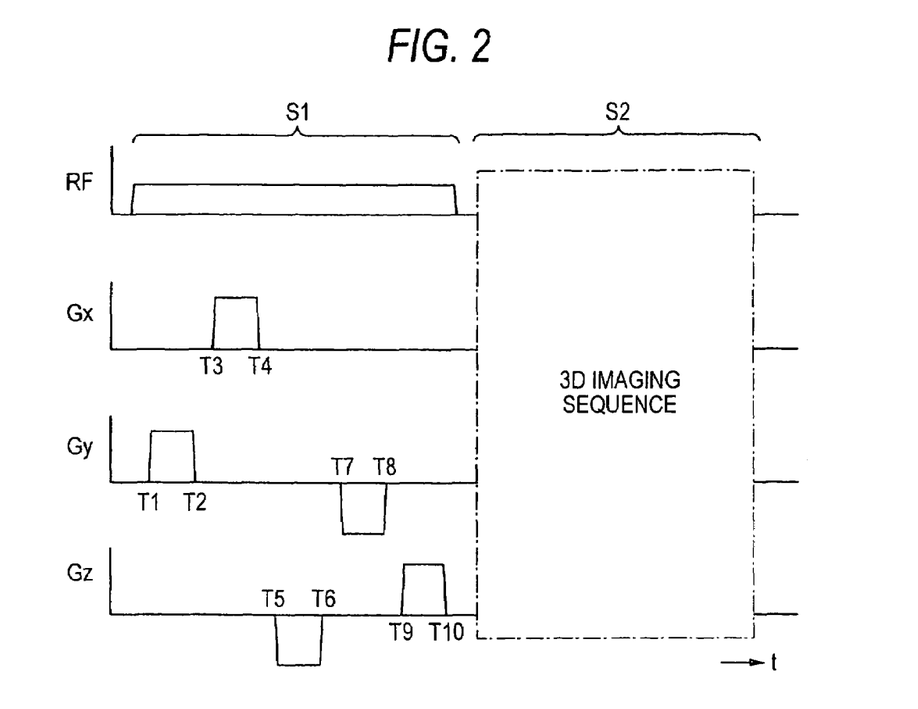
FIG. 2 shows a pulse sequence showing control signals for magnetic tagging in the first embodiment of the invention (which sequence also explains a procedure for magnetic tagging, stored as a magnetic resonance imaging program according to the invention)

Owing to this program, for example, as shown in FIG. 2 to be described later the magnetic resonance diagnosis apparatus is allowed to execute a step S1 of conducting magnetic tagging in a predetermined three-dimensional region of the object and a step S2 of collecting MR signals from a region containing the three-dimensional region that is magnetically tagged. In this embodiment, the control unit 11 functionally accomplishes control means (magnetic tagging means and signal collection means) of the invention.

Incidentally, the pulse sequence will be described later in detail. This program may be installed in advance before shipment of the MRI apparatus or may be installed after shipment of the MRI apparatus through a communication line such as the Internet, whenever necessary. The X-Y-Z axes gradient magnetic coil 2 and the transmission/reception coil 3 generate the X, Y and Z gradient magnetic fields and the radio frequency magnetic field, respectively.

The transmission/reception coil 3 receives the MR signals from the object P and transmits the reception signals to the control unit 11 through the receiver 6. The control unit 11 executes a predetermined signal processing, generates a tomogram of the object and displays it on the display unit 12.

Next, the pulse sequence using the magnetic tagging method of this embodiment will be explained.

As described above, the magnetic tagging method transmits the radio frequency magnetic field to only a part of the imaging region of the object P to bring it into magnetic saturation and then performs imaging. Incidentally, the pulse sequence for magnetically saturating a part of the imaging region will be hereby called particularly "control signals for magnetic tagging" and the pulse sequence transmitted to image the imaging region after the transmission of the control signals for magnetic tagging will be called "imaging pulse sequence".

FIG. 2 is a graph showing the timings of the controls signals transmitted to the transmitter 5, the X-axis gradient magnetic field power source 7, the Y-axis gradient magnetic field power source 8 and the Z-axis gradient magnetic field power source 9, respectively.

Incidentally, the abscissa of FIG. 2 represents the time and the ordinate does the magnitude of the control signal. Symbol RF in FIG. 2 represents the control signal for magnetic tagging that is transmitted to the transmitter 5 and symbols $G_x$, $G_y$ and $G_z$ represent the control signals for magnetic tagging that are transmitted to the X-axis gradient magnetic field power source 7, the Y-axis gradient magnetic field power source 8 and the Z-axis gradient magnetic field power source 9 (control signal for X-axis magnetic tagging, control signal for Y-axis magnetic tagging and control signal for Z-axis magnetic tagging), respectively. It will be assumed that a "plus" direction of the magnitude of the control signal for magnetic tagging transmitted to each gradient magnetic field power source represents the direction of each axis (for example, the X-axis direction is "plus" in the case of the control signal for X-axis magnetic tagging) and a "minus direction" represents the direction opposite to each axis (for example, the direction opposite to the X-axis direction is "minus" in the case of the control signal for X-axis magnetic tagging).

The control signal for magnetic tagging in this embodiment transmits five times in total the X-axis magnetic tagging pulse, the Y-axis magnetic tagging pulse and the Z-axis magnetic tagging pulse (corresponding to the step S2 described above) while the RF pulses are transmitted at a predetermined intensity. In other words, the control signals are transmitted five times to each gradient magnetic field power source as described above.

The magnetic tagging pulses are serially applied in the following sequence. Namely, the Y-axis magnetic tagging pulse of a predetermined magnitude is transmitted in the pulse direction for the time T1 to T2. Next, the X-axis magnetic tagging pulse of a predetermined magnitude is applied in the pulse direction for the time T3 to T4 after the passage of a predetermined time. Subsequently, the Z-axis magnetic tagging pulse of a predetermined magnitude is applied in the minus direction for the time T5 to T6 and the Y-axis magnetic tagging pulse of a predetermined magnitude is applied in the minus direction for the time T7 to T8. The Z-axis magnetic tagging pulse of a predetermined magnitude is applied in the plus direction for the time T9 to T10.

Incidentally, the magnitude of the magnetic tagging pulse transmitted to each gradient magnetic field is substantially equal to each other. Each pulse is applied substantially equidistantly time-wise (for example, the interval T2 to T3 is equal to the interval T4 to T5) and the application time of each pulse (for example, 1 ms) is also substantially equal (for example, T1 to T2 is equal to T3 to T4).

Figure 3:
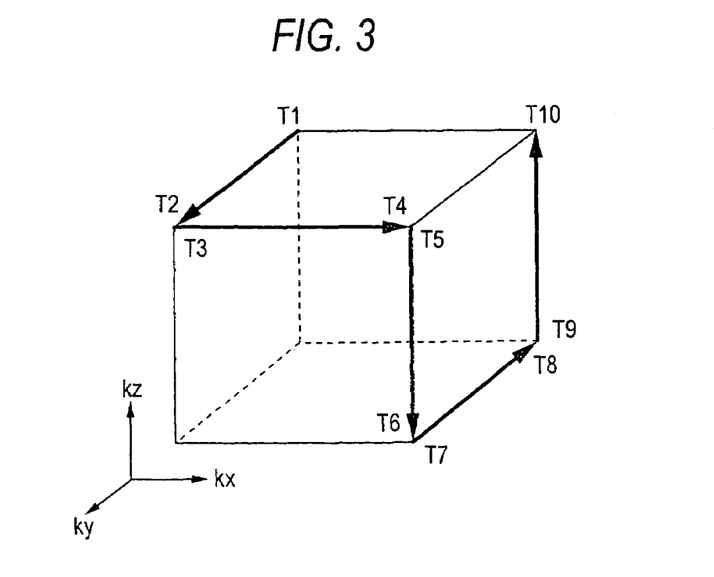
FIG. 3 is an explanatory view useful for explaining a behavior of magnetization in a k-space by the control signal for magnetic tagging in the first embodiment of the invention.

FIG. 3 shows a state of a k-space under such a control signal for magnetic tagging.

In FIG. 3, magnetization M moves in a ky direction from time T1 to T2, in a kx direction from time T3 to T4, in a −kz direction from T5 to T6, in a −ky direction from time T7 to T8 and in a kz direction from time T9 to T10. Incidentally, in FIG. 3, the orbit of magnetization M is indicated by thick arrows.

In other words, magnetization M moves on the sides of a three-dimensional cube in the k-space and this means that three-dimensional tagging is conducted.

Figure 4A:
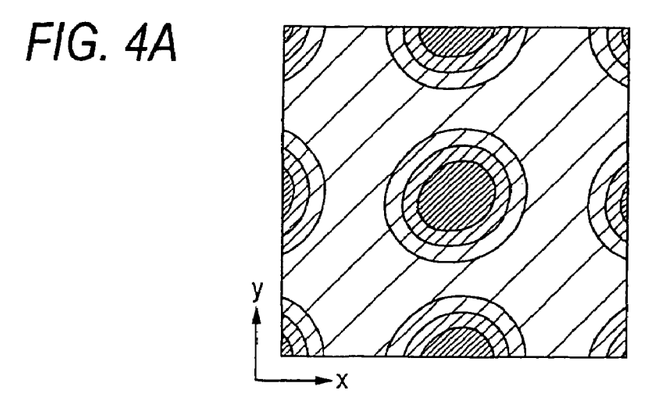
FIGS. 4A to 4C are schematic views each showing an intensity distribution of magnetization M magnetically tagged in the first embodiment.
Figure 4B:
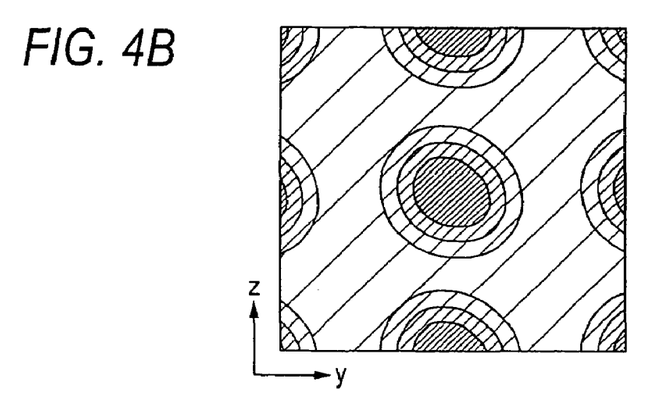
Figure 4C:
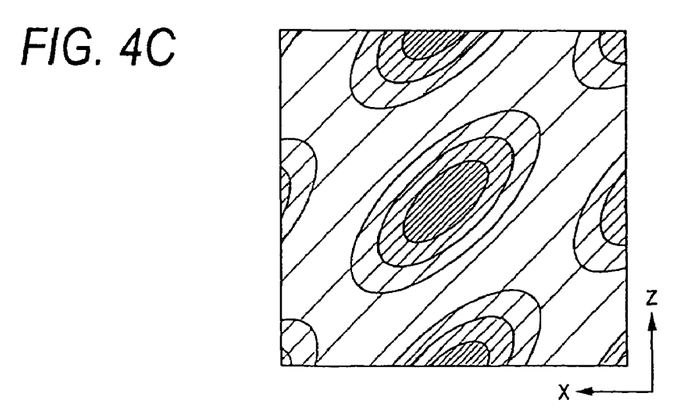

FIGS. 4A to 4C schematically show the intensity distribution of magnetization M magnetically tagged (excited) in an actual space. Additionally, in FIGS. 4A to 4C, the behavior of magnetization M can be calculated by using the following Bloch equation.

$$(dM/dt) = \gamma M \times H - (M_z - M_o)/T_1 \times k - (M_x i + M_y j)/T_2$$

Figure 5:
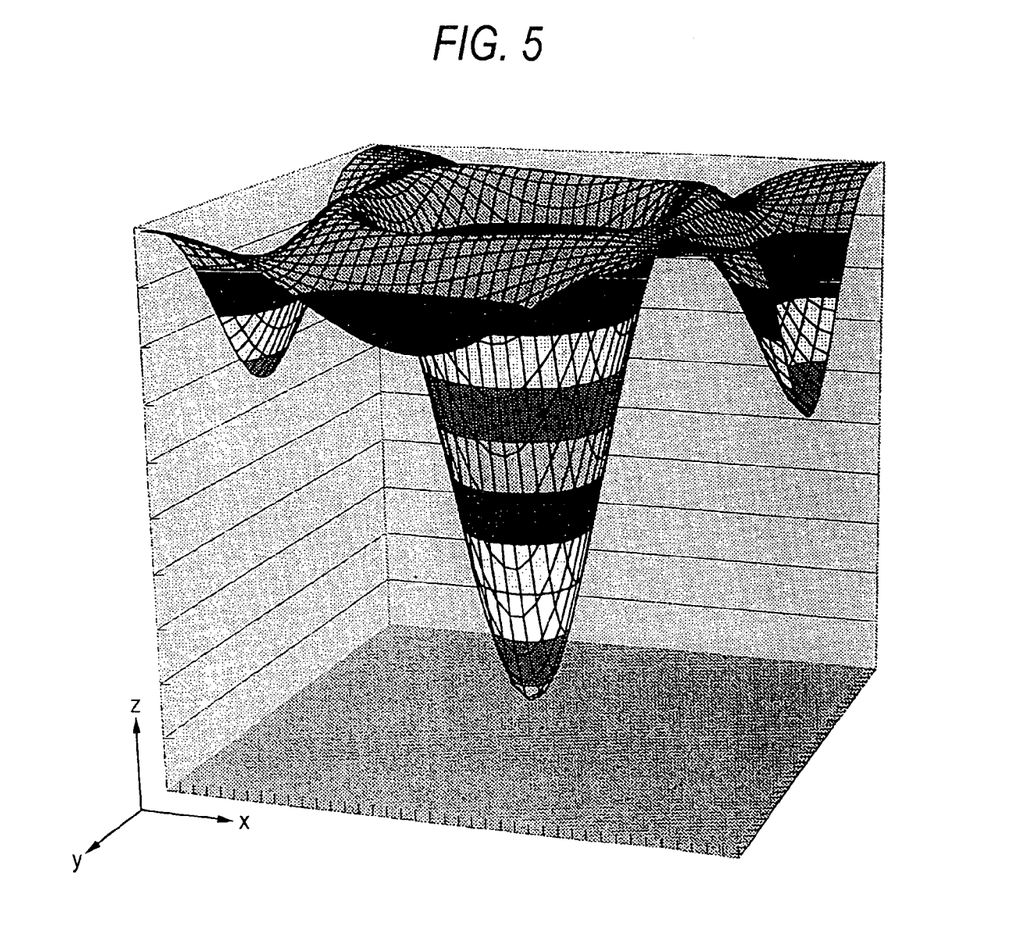
FIG. 5 is a graph showing an intensity distribution of an X-Y section of magnetization M magnetically tagged in the first embodiment.

Here, M represents magnetization. H represents the magnetic field and i, j and k represent unit vectors in the x, y and z directions, respectively. Mx, $M_y$ and $M_z$ represent x, y and z components of magnetization, respectively. Mo represents an initial value of magnetization. $T_1$ and $T_2$ represent longitudinal relaxation time and a transverse relaxation time, respectively. FIG. 4A shows the X-Y section. FIG. 4B shows the Y-Z section. FIG. 4C shows the X-Z section. The intensity of magnetization M is represented by the contour line and by the density of hatching (the closer to the center of the contour distribution, the lower becomes the intensity of magnetization M (excitation)). FIG. 5 cubically shows the intensity distribution of the X-Y section, in particular. As is obvious from FIG. 5, the portion having the lowest intensity (excitation) exists at the center and portions having lower intensities repeatedly exist in the x and y directions from the center portion in predetermined intervals.

This repetition pitch becomes narrower as the orbit described by magnetization M in the k-space becomes greater. In other words, when the magnitude of the gradient magnetic field pulse is increased, the repetition pitch becomes small and the excited area becomes small. When the orbit described by magnetization M in the k-space is decreased, the repetition pitch becomes broad and the excited area becomes great.

After the control signal for magnetic tagging described above is transmitted to the transmitter 5 and to each gradient magnetic field power source 7 to 9, the imaging pulse sequence (corresponding to the MR signal collection step S2 described above) is transmitted. Consequently, it is possible to distinguish the portion that is magnetically tagged and to conduct imaging.

Incidentally, a multi-slice method for collecting three-dimensional data and a 3D volume imaging method are preferred for the imaging pulse sequence but a spin echo (SE) method, a gradient echo (GRE) method and fast spin echo (FSE) may also be used.

In this embodiment, the control signal for magnetic tagging is applied so that the orbit of magnetization in the k-space passes at least one of the four sides on each surface of the cubic as the method for conducting magnetic tagging. Therefore, a three-dimensional region approximate to a sphere can be magnetically tagged. Control is easy because the magnitude of each magnetic gradient field pulse and the application time are the same in magnetic tagging.

Since the RF pulse keeps a substantially constant intensity during magnetic tagging, means for establishing the application timings of the RF pulses is not necessary and control becomes further easier.

When the RF pulse is applied whenever the gradient magnetic field pulse in each direction is applied, the rise time and the fall time of the RF pulse are necessary each time. However, when the intensity of the RF pulse is kept substantially constant during magnetic tagging as shown in FIG. 2, the time necessary for the rise and fall of the RF pulse at intermediate parts other than both ends can be saved. In consequence, the time for magnetic tagging can be shortened and eventually, the overall imaging (scanning) time can be shortened.

Second Embodiment

Figure 6:
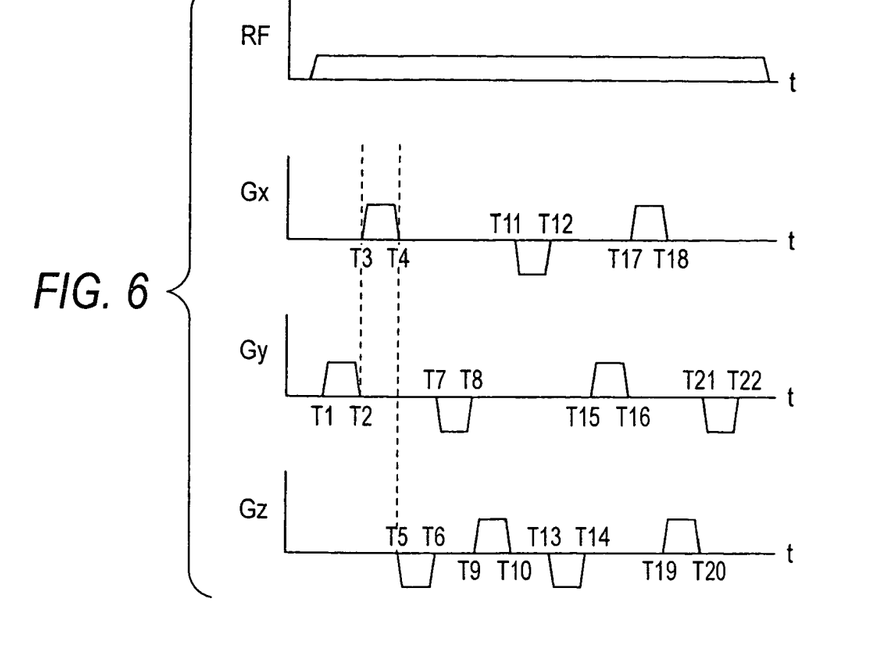
FIG. 6 shows a pulse sequence showing control signals for magnetic tagging in a second embodiment of the invention.

The second embodiment of the invention will be hereinafter explained with reference to the drawings. This embodiment is different from the first embodiment in that the control signal for magnetic tagging is different. FIG. 6 is a graph showing the control signal for magnetic tagging in this embodiment. Since the reference numerals and signs are the same as those in FIG. 2, the detail will be hereby omitted.

While the RF pulse is transmitted at a predetermined intensity, the control signal for magnetic tagging in this embodiment transmits 11 times in total the control signals for X-axis magnetic tagging, Y-axis magnetic tagging and Z-axis magnetic tagging.

The control signals for magnetic tagging transmitted 11 times to each gradient magnetic field power source are serially as follows. Namely, the Y-axis magnetic tagging pulse of a predetermined magnitude is transmitted in the plus direction for the time T1 to T2. Next, the X-axis magnetic tagging pulse of a predetermined magnitude is applied in the plus direction for the time T3 to T4 after the passage of a predetermined time. Subsequently, the Z-axis magnetic tagging pulse of a predetermined magnitude is applied in the minus direction for the time T5 to T6 and the Y-axis magnetic tagging pulse of a predetermined magnitude is applied in the minus direction for the time T7 to T8. The Z-axis magnetic tagging pulse of a predetermined magnitude is applied in the plus direction for the time T9 to T10. The X-axis magnetic tagging pulse of a predetermined magnitude is applied in the minus direction for the time T11 to T12 and the Z-axis magnetic tagging pulse of a predetermined magnitude is applied in the minus direction for the time T13 to T14. The Y-axis magnetic tagging pulse of a predetermined magnitude is applied in the plus direction for the time T15 to T16. The X-axis magnetic tagging pulse of a predetermined magnitude is applied in the plus direction for the time T17 to T18 and the Z-axis magnetic tagging pulse of a predetermined magnitude is applied in the plus direction for the time T19 to T20. The Y-axis magnetic tagging pulse of a predetermined magnitude is applied in the minus direction for the time T21 to T22. Incidentally, the magnitude of the magnetic tagging pulse of each gradient magnetic field, the pulse interval and the application time of each pulse are the same as those of the first embodiment.

Figure 7:
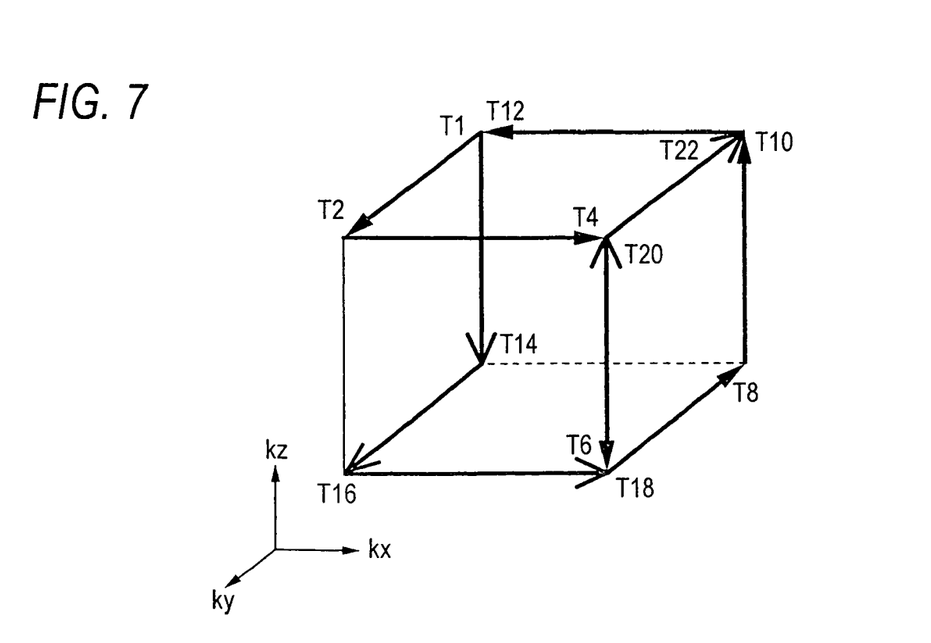
FIG. 7 is an explanatory view useful for explaining a behavior of magnetization in a k-space by control signals for magnetic tagging in the second embodiment.

FIG. 7 shows the state in the k-space under such a control signal for magnetic tagging.

In FIG. 7, magnetization M moves on the predetermined sides of the cube from T1 to T12 during the time T1 to T22 and returns to its original position in the k-space (to the state after making a round). The orbit of magnetization M moves on the same sides of the cube in the time T5 to T6 and T19 to T20. Incidentally, in FIG. 7, the orbit of the first round is indicated by arrows having a thick distal end and the orbit of the second round, by arrows having a thin distal end.

Figure 8A:
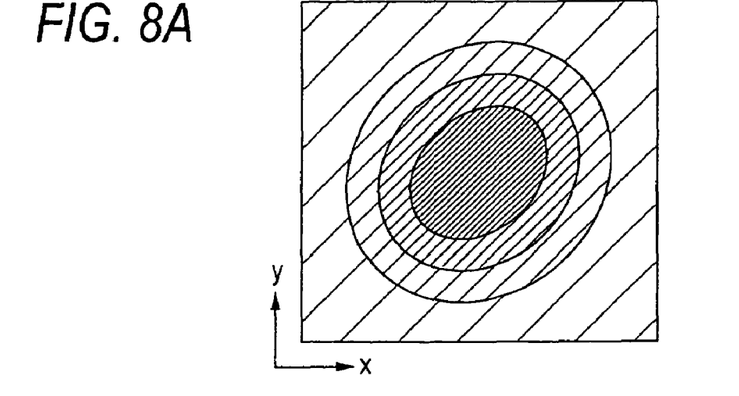
FIGS. 8A to 8C are schematic views each showing an intensity distribution of magnetization M magnetically tagged in the first embodiment.
Figure 8B:
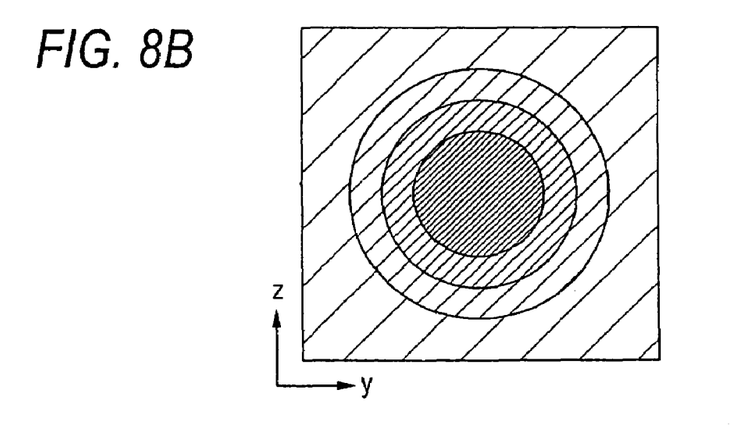
Figure 8C:
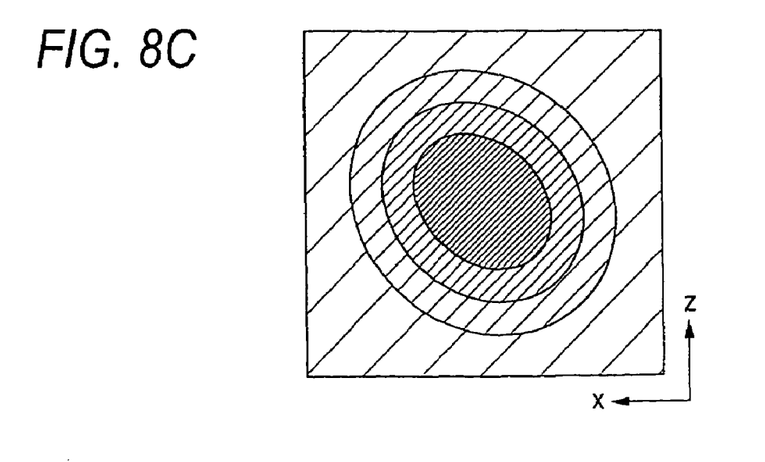

FIGS. 8A to 8C schematically show the behavior of magnetization M calculated by the following BLOCH equation in the same way as in the first embodiment.

Since the rest of the constructions and the operation are the same as those of the first embodiment, the explanation will be hereby omitted.

This embodiment applies the gradient magnetic pulses so that the orbit of magnetization in the k-space becomes three-dimensional as the method for conducting magnetic tagging in the same way as in the first embodiment, and can therefore perform three-dimensional magnetic tagging. Since the magnitude of each gradient magnetic field pulse and the application time in magnetic tagging are equidistant in the same way as in the first embodiment, control is easy.

Since the RF pulse keeps a substantially constant intensity during magnetic tagging in the same way as in the first embodiment, means for establishing the application timing of the RF pulse is not necessary and control becomes further easier.

Particularly in this embodiment, the orbit of magnetization M passes by at least once (makes a round) all the apexes of the cube in the k-space. Because magnetization M is moved much more in the three-dimensional space in this way, the intensity distribution of magnetization in this embodiment can be brought closer to a circle in each section in comparison with the intensity distribution of magnetization in the first embodiment. In other words, it is possible to lower the degree of flatness of the excitation area and to bring it closer to the sphere. Incidentally, the closer the excitation area to the sphere, the more uniform becomes magnetic tagging in each section, and this is a desirable form. In the first embodiment, on the other hand, the three-dimensional orbit is described lest magnetization M overlaps in the k-space. Therefore, three-dimensional magnetic tagging becomes possible in a shorter pulse sequence and the first embodiment is effective in imaging that needs the stop of breathing.

Third Embodiment

The third embodiment of the invention will be explained with reference to the drawings. This embodiment is different from the first embodiment in that the application amount of each pulse in the control signal for magnetic tagging can be changed. Here, the term "application amount of pulse" means the product of the magnitude of the pulse and its time.

Figure 9:
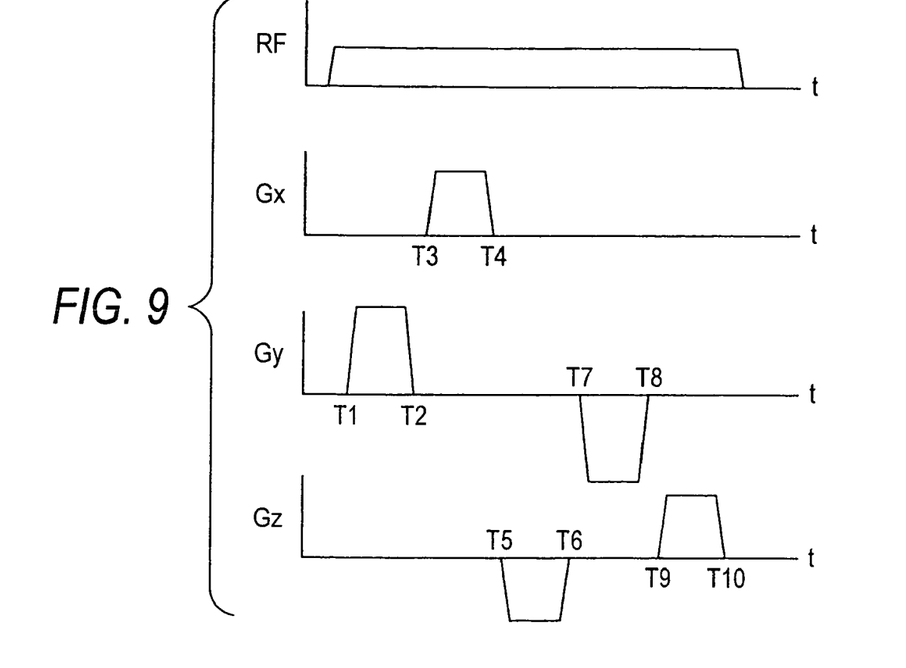
FIG. 9 shows a pulse sequence showing control signals for magnetic tagging in the second embodiment of the invention.

As a concrete construction, means for changing the magnitude of the gradient magnetic field pulse (not shown) during magnetic tagging is arranged in the control unit 11 shown in FIG. 1. FIG. 9 is a graph showing the control signal for magnetic tagging in this embodiment. Since the detail of reference numerals and signs are the same as those of FIG. 2, the explanation will be hereby omitted.

Figure 10:
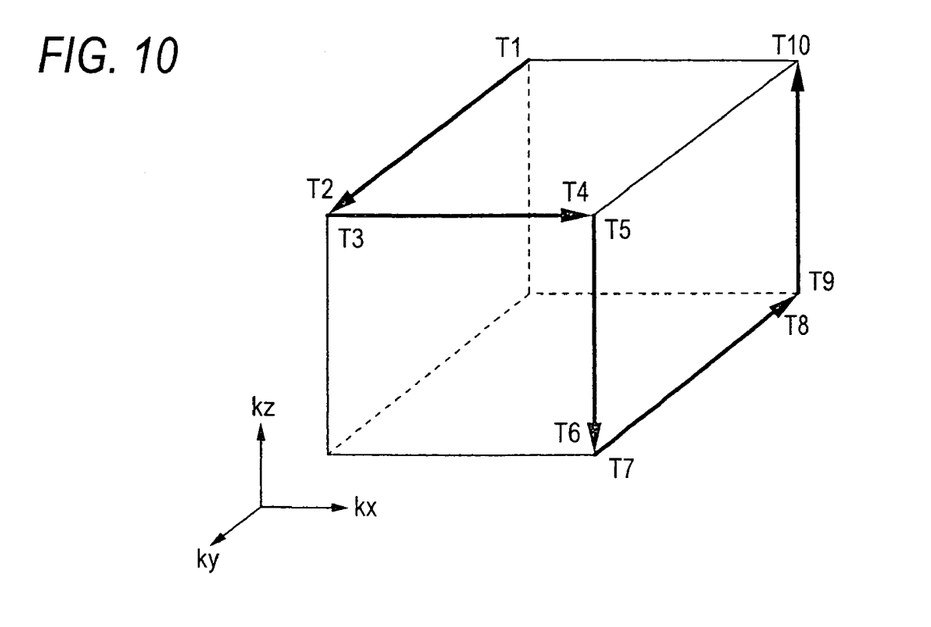
FIG. 10 is an explanatory view useful for explaining a behavior of magnetization in a k-space by control signal for magnetic tagging in a third embodiment.

FIG. 10 shows the state of the k-space in this embodiment. The operator inputs the shape of the orbit that the orbit of magnetization describes in the k-space, through the input unit 10. A cube, a rectangle, a sphere and other polyhedrons can be selected as a default value. Incidentally, the following explanation will be given on the assumption that the shape that provides the rectangle as the orbit of magnetization in the k-space is selected.

When the operator inputs the shape described above, the control unit 11 applies the control signals for magnetic tagging shown in FIG. 9. In order for magnetization to describe the rectangular orbit in the k-space, the magnitude of the control signal for Y-axis magnetic tagging among the control signal for the X-axis magnetic tagging, the control signal for the Y-axis magnetic tagging and the control signal for the Z-axis magnetic tagging is different in the control signals for magnetic tagging in this embodiment. As for the magnitude of the pulses of the control signals for magnetic tagging in this embodiment, the pulse transmitted from the time T1 to T2 and the pulse transmitted from the time T7 to T8 are greater than other pulses. Therefore, as shown in FIG. 10, the orbit of magnetization describes the same length in the kx and kz directions but a longer obit in the ky direction than the length in the kx direction.

Since the transmission sequence of the pulses in the control signals for magnetic tagging is the same as that of the first embodiment, the explanation will be hereby omitted. The rest of the constructions and the operation are also the same as those of the first embodiment, the explanation will be hereby omitted.

In this embodiment, the gradient magnetic field pulse is applied so that the orbit of magnetization in the k-space becomes three-dimensional in the same way as in the first embodiment and consequently, three-dimensional magnetic tagging is possible. Since the application time of each gradient magnetic field pulse is equidistant in magnetic tagging in the same way as in the first embodiment, control is easy. Since the RF pulse keeps a substantially constant intensity during magnetic tagging in the same way as in the first embodiment, means for establishing the application timings of the RF pulses is not necessary and control becomes further easier. Particularly because means for changing the application amount of each gradient magnetic field pulse during magnetic tagging is disposed, the repetition pitch of the excitation region in each direction can be changed.

Particularly because this embodiment employs the method for changing the magnitude of the pulse as the means for changing the application amount of the pulse, the region to be magnetically tagged can be changed without extending time-wise the pulse sequence. A method that changes the application time of the pulse may also be used as the means for changing the application amount of the pulse.

The first to third embodiments described above are based on the assumption that the RF pulses are transmitted substantially at a predetermined intensity for a predetermined time when magnetic tagging is conducted but the RF pulses may also be transmitted intermittently between the pulses transmitted to the gradient magnetic field power sources. When the RF pulses are intermittently transmitted, however, means for establishing the transmission timings of the RF pulses becomes necessary but when the RF pulses are continuously transmitted, the means for establishing the timing is not necessary, in particular. Therefore, the transmission of the RF pulses at the predetermined intensity for the predetermined time has the advantage that the apparatus can be simplified.

The magnitude of the gradient magnetic field pulses in magnetic tagging, their interval and their application time are not limited to those described in the embodiments described above but may be those which make the orbit of magnetization three-dimensional in the k-space.

In the embodiments described above, the orbit described by magnetization during magnetic tagging is cubic and rectangular, in particular, but the shape may also be a sphere or other polyhedron.

The embodiments given above have particularly been described about the cylindrical gantry but they can likewise be applied to an open type gantry in which the static magnetic field is applied substantially vertically with respect to the body axis direction of the object P.

Incidentally, the invention can be executed by combining the embodiments described above with one another.

INDUSTRIAL APPLICABILITY

As explained above in detail, the invention can perform magnetic tagging of the three-dimensional region and can therefore provide an MRI apparatus that can more flexibly observe the motion of organs and the flow of the blood.

What is claimed is:

1. A magnetic resonance diagnosis apparatus comprising:
   static magnetic field generation means for generating a static magnetic field to be applied to an object;
   gradient magnetic field generation means for generating gradient magnetic fields to be applied to said object;
   radio frequency magnetic field generation means for generating a radio frequency magnetic field to be applied to said object; and
   control means for controlling said gradient magnetic field generation means and said radio frequency magnetic field generation means;
   wherein said control means includes:
      magnetic tagging means for magnetically tagging a predetermined three-dimensional region of the object by controlling the gradient magnetic fields such that magnetization inside said object due to the gradient magnetic fields describes a three-dimensional movement orbit inside k-space; and
      signal collection means for collecting MR signals from a region of said object inclusive of said magnetically tagged three-dimensional region.

2. A magnetic resonance diagnosis apparatus according to claim 1, wherein;
   the radio frequency magnetic field is controlled so that said radio frequency magnetic field is kept at a predetermined intensity while said gradient magnetic fields are controlled.

3. A magnetic resonance diagnosis apparatus according to claim 1, wherein said magnetic tagging means controls the gradient magnetic fields so that said magnetization describes, as the three-dimensional movement orbit, an orbit moving on predetermined sides of a substantially cube-shaped volume in k-space.

4. A magnetic resonance diagnosis apparatus according to claim 3, wherein said magnetic tagging means controls the gradient magnetic fields so that said magnetization moves a plurality of times on at least one of said predetermined sides of a substantially cubical volume in k-space.

5. A magnetic resonance diagnosis apparatus according to claim 1, wherein said magnetic tagging means controls the gradient magnetic fields so that said magnetization describes, as the three-dimensional movement orbit, an orbit moving on predetermined sides of a substantially rectangularly-shaped volume in k-space.

6. A magnetic resonance diagnosis apparatus according to claim 1, wherein said magnetic tagging means controls the gradient magnetic fields so that said magnetization describes, as the three-dimensional movement orbit, an orbit moving on predetermined sides of a polyhedron-shaped volume in k-space.

7. A magnetic resonance diagnosis apparatus according to claim 1, wherein said magnetic tagging means controls the gradient magnetic fields so that said magnetization describes, as the three-dimensional movement orbit, an orbit moving on a surface of a substantially spherically-shaped volume in k-space.

8. A magnetic resonance diagnosis apparatus comprising:
static magnetic field generation means for generating a static magnetic field to be applied to an object;
gradient magnetic field generation means for generating gradient magnetic fields to be applied to said object;
radio frequency magnetic field generation means for generating a radio frequency magnetic field to be applied to said object; and
control means for controlling said gradient magnetic field generation means and said radio frequency magnetic field generation means;
wherein said control means includes:
magnetic tagging means for controlling operations of both said gradient magnetic field generation means and said radio frequency magnetic field generation means to magnetically tag a predetermined three-dimensional region of said object such that magnetization inside said object due to the gradient magnetic fields describes a three-dimensional movement orbit inside k-space; and
signal collection means for collecting MR signals from a region of said object inclusive of said magnetically tagged three-dimensional region.

9. A magnetic resonance signal collection method for collecting MR signals from an object by applying gradient magnetic fields and a radio frequency magnetic field to the object placed in a static magnetic field to obtain an image, said method comprising:
controlling both said gradient magnetic fields and said radio frequency magnetic field to magnetically tag a predetermined three-dimensional region of the object such that magnetization inside said object due to the gradient magnetic fields describes a three-dimensional movement orbit inside k-space; and
collecting said MR signals from a region of the object inclusive of said magnetically tagged three-dimensional region for creating said image.

10. A magnetic resonance signal collection method according to claim 9, wherein said radio frequency magnetic field is controlled to keep a predetermined intensity while said magnetic tagging is performed.

11. A magnetic resonance signal collection method according to claim 9, wherein said magnetic tagging is performed while said gradient magnetic fields are controlled to cause said magnetization to move on predetermined sides of a substantially cube-shape volume in k-space.

12. A magnetic resonance signal collection method according to claim 9, wherein said magnetic tagging is performed while said gradient magnetic fields are controlled to cause said magnetization to move on predetermined sides of a substantially rectangularly-shaped volume in k-space.

13. A computer-readable program storage medium having stored therein a computer program for use in computerized magnetic resonance imaging diagnosis apparatus to create an image, said use causing the apparatus to perform a process including:
causing the magnetic resonance diagnosis apparatus to perform magnetic tagging for a predetermined three-dimensional region of an object such that magnetization inside said object due to gradient magnetic fields describes a three-dimensional movement orbit inside k-space; and
causing said magnetic resonance diagnosis apparatus to collect MR signals from a region of the object inclusive of said magnetically tagged three-dimensional region for creating said image.

14. A magnetic resonance diagnosis apparatus comprising:
a static magnetic field generating unit configured to generate a static magnetic field to be applied to an object;
a gradient magnetic field generating unit configured to generate gradient magnetic fields to be applied to said object;
a radio frequency magnetic field generating unit configured to generate a radio frequency magnetic field to be applied to said object;
a magnetic tagging unit configured to magnetically tag a predetermined three-dimensional region of the object such that magnetization inside said object due to gradient magnetic fields describes a three-dimensional movement orbit inside k-space by controlling both the gradient magnetic field generating unit and the radio frequency magnetic field generating unit in a predetermined sequence; and
a signal collection unit configured to collect MR signals from a region of said object inclusive of the magnetically tagged three-dimensional region after the magnetic tagging.

15. An apparatus according to claim 14, wherein the magnetic tagging unit is configured to magnetically tag the predetermined three-dimensional region of the object by controlling the gradient magnetic field generating unit so as to generate the gradient magnetic fields providing magnetization inside the object to describe a three-dimensional movement orbit in k-space.

16. An apparatus according to claim 15, wherein the radio frequency magnetic field generation unit is controlled so that the radio frequency magnetic field is kept at a predetermined intensity while said gradient magnetic fields are controlled to change.

17. An apparatus according to claim 16, wherein the three-dimensional movement orbit is an orbit moving on predetermined sides of a polyhedron in k-space.

18. An apparatus according to claim 17, wherein the polyhedron is substantially cube-shaped.

19. An apparatus according to claim 17, wherein the polyhedron is substantially rectangularly shaped.

20. An apparatus according to claim 17, wherein the three-dimensional movement orbit is an orbit moving a plurality of times on at least one predetermined side of the polyhedron in k-space.

21. An apparatus according to claim 16, wherein the three-dimensional movement orbit is an orbit moving on a surface of a substantially spherical shape in k-space.

* * * * *